(12) United States Patent
Wenzel et al.

(10) Patent No.: US 7,449,115 B2
(45) Date of Patent: Nov. 11, 2008

(54) METHOD FOR THE ACCELERATED DIALYTIC RECOVERY OF FOREIGN SUBSTANCES FROM PASSIVE COLLECTORS CONSISTING OF SEMIPERMEABLE MEMBRANES HAVING DIFFERENT DIMENSIONS

(75) Inventors: Klaus-Dieter Wenzel, Taucha (DE); Branislav Vrana, Portsmouth (GB); Andreas Hubert, Leipzig (DE); Brigitta Mothes, Leipzig (DE); Marion Heinrich, Leipzig (DE); Gerrit Schueuermann, Threna (DE)

(73) Assignee: UFZ-Umweltforschungs Zentrum Leipzig-Halle GmbH, Leipzig (DE)

( * ) Notice: Subject to any disclaimer, the term of this patent is extended or adjusted under 35 U.S.C. 154(b) by 348 days.

(21) Appl. No.: 10/512,543

(22) PCT Filed: Apr. 25, 2003

(86) PCT No.: PCT/EP03/04320

§ 371 (c)(1), (2), (4) Date: Sep. 14, 2005

(87) PCT Pub. No.: WO03/090909

PCT Pub. Date: Nov. 6, 2003

(65) Prior Publication Data
US 2006/0086665 A1 Apr. 27, 2006

(30) Foreign Application Priority Data
Apr. 26, 2002 (DE) ................. 102 19 554

(51) Int. Cl.
 B01D 11/00 (2006.01)
 B01D 61/00 (2006.01)
 B01D 59/26 (2006.01)
 B01D 39/00 (2006.01)
 B01D 63/00 (2006.01)

(52) U.S. Cl. ............... 210/634; 210/638; 210/644; 210/908; 210/909; 210/502.1; 96/153; 96/413

(58) Field of Classification Search .......... 210/634, 210/638, 644, 502.1, 908, 909; 96/153, 413; 29/458

See application file for complete search history.

(56) References Cited

U.S. PATENT DOCUMENTS

| 4,269,804 | A | 5/1981 | Kring |
| 5,098,573 | A | 3/1992 | Huckins et al. |
| 5,395,426 | A | 3/1995 | Huckins et al. |
| 6,226,852 | B1 * | 5/2001 | Gundel et al. ............. 29/458 |

(Continued)

OTHER PUBLICATIONS

Huckins et al: "Polymeric Film Dialysis in Organic Solvent Media for Cleanup of Organic Contaminants." J. Assoc. Off. Anal. Chem. (vol. 73, No. 2, 1990), pp. 290-293+.

(Continued)

*Primary Examiner*—Ana M Fortuna
(74) *Attorney, Agent, or Firm*—Millen, White, Zelano & Branigan, P.C.

(57) ABSTRACT

The invention relates to a dialysis method of recovering foreign substances, particularly low-molecular weight inorganic and/or organic substances, from semipermeable membrane of varying length and dimensions, using a PLE (pressurized liquid extraction) apparatus. The membranes are preferably in the form of a tube, for example semipermeable membrane devices (SPMDs) which, in the form of passive samplers, accumulate foreign substances/pollutants on an absorbent or adsorbent.

21 Claims, 2 Drawing Sheets

U.S. PATENT DOCUMENTS

2006/0086665 A1* 4/2006 Wenzel et al. ............... 210/644

OTHER PUBLICATIONS

Huckins et al.: "Lipid-Containing Semipermeable Membrane Devices for Monitoring Organic Contaminants in Water." Environ. Sci. Technol. 1992, pp. 2489-2496.

Richard Brown: "Monitoring the Ambient Environment With Diffusive Samplers Theory and Practical Considerations." J. Environ. Monit., 2000, pp. 1-9.

Schlusener M P et al: "Determination of Antibiotics From Soil by Pressurized Liquid Extraction and Liquid Chromatography-Tandem Mass Spectrometry", Journal of Chromatography A, Elsevier Science, NL, vol. 1003, NR. 1-2, pp. 21, 28.

* cited by examiner

METHOD FOR THE ACCELERATED DIALYTIC RECOVERY OF FOREIGN SUBSTANCES FROM PASSIVE COLLECTORS CONSISTING OF SEMIPERMEABLE MEMBRANES HAVING DIFFERENT DIMENSIONS

The invention relates to a dialysis method of recovering foreign substances, particularly low-molecular weight inorganic and/or organic substances, from passive samplers, using pressurized liquid extraction (PLE). The passive samplers are comprised of semipermeable membranes of varying length and dimensions. More specifically, the dialysis method is used in the trace-analytical detection of semivolatile to low volatile organic pollutants, e.g. chloroorganic pesticides, polychlorinated biphenyls and other chloroorganics, as well as polycyclic aromatic hydrocarbons (PAH). The membranes are preferably semipermeable membrane devices (SPMDs) which, in the form of passive samplers, accumulate foreign substances/pollutants on an absorbent or adsorbent. Alternatively, the pollutants to be dialyzed may also come from sediment, soil, old waste, vegetable or other matrices which are placed in semipermeable membranes in order to remove higher-molecular weight matrix components from a pollutant extract, in which case no absorbent/adsorbent is required. The dialysis method using a PLE apparatus is highly efficient, substantially speeding up the dialysis of pollutants from semipermeable membranes.

SPMDs are preferably used in environmental monitoring as an innovative passive sampler technology for detection and assessment of trace concentrations of semivolatile organic pollutants (SVOCs). Said passive samplers represent a useful alternative to the well-known, but complex active samplers. They allow the determination of time-weighted average (TWA) concentrations over substantial periods of time. Further, the cost of such sampling equipment is substantially lower compared to active samplers, and no power supply is required. Passive samplers are used on a larger scale in monitoring the work-place atmosphere, where the issue preferably is detecting volatile organic pollutants in the ambient air. However, the use of passive samplers in outdoor air monitoring is relatively new. Recently, Brown R. H. [(2000): Monitoring the Ambient Environment with Diffusive Samplers: Theory and Practical Considerations. Journal of Environmental Monitoring 2, 1-9] has published a first review on the potential of diffusive samplers in monitoring the outdoor air quality.

It was only in recent years that publications on the subject of utilizing the passive sampling technology in monitoring semivolatile organic pollutants in ambient air appeared to a minor extent. Tested passive samplers include wax-coated paper filters, fat-coated glass plates or glass fiber filters, glass plates and textiles coated with stationary GC phase. In general, passive samplers having a high surface-to-volume ratio, referred to as "badge type" in the English literature, have been constructed in order to accumulate a sufficient quantity of pollutants from the atmosphere within a practicable period of measurement. Such samplers represent a potential instrument to accumulate gaseous pollutants from the air and estimate their concentration in the air. In "badge type" configurations, however, there is a potential risk that the accumulation kinetics would depend on the wind speed if the sampling medium is in direct contact with the atmosphere.

In environmental monitoring the SPMDs are among the integrative passive samplers of atmospheric and waterborne pollutants. Commercially available SPMDs consist of a tubular polyethylene membrane of small thickness (75-90 μm), which includes a thin film of the neutral synthetic lipophilic fatty acid ester triolein (high molecular weight of >600 Da) in the interior thereof. Lipophilic chemical substances, e.g. the chloroorganic compounds HCH isomers, polychlorinated biphenyls, chlorobenzenes, p,p'-DDT and its degradation products p,p'-DDE and p,p'-DDD, as well as PAHs, are capable of diffusing through said semipermeable membrane, being accumulated or concentrated there in a lipid fatty acid ester, i.e., the triglyceride triolein. This ensures detection of environmentally relevant pollutant analytes on a trace level. The SPMD technology (U.S. Pat. No. 5,098,573) thus allows determination of time-averaged concentrations of persistent organic compounds dissolved in bodies of water and transported in the atmosphere in the form of gases.

Initially, the method introduced by Huckins et al. [Huckins, J. N.; Manuweera, G. K.; Petty, J. D.; Mackay, D.; Lebo, J. A. (1993): Lipid-containing Semipermeable Membrane Devices for Monitoring Organic Contaminants in Water. Environ. Sci. Technol. 27, 2489-2496.] has been developed to detect pollution of aquatic systems by lipophilic organic pollutants. It has later been demonstrated that SPMDs can also be used in air monitoring of gaseous residues such as PCBs, chloroorganic pesticides and polycyclic aromatic hydrocarbons.

The use of said SPMD technology involves the disadvantage of time-consuming sample treatment (about 48 hours) and comparatively high consumption of solvents (520 ml) per standard SPMD tube (length: 91 cm) in dialytic recovery of organic substances accumulated on triolein (U.S. Pat. No. 5,395,426). To date, according to the state of science, each SPMD tube is initially dialyzed for 24 hours in 260 ml of n-hexane as solvent. Thereafter, the solvent is replaced by fresh solvent, and the sample is dialyzed for another 24 hours [Huckins, J. N.; Tubergen, M. W.; Lebo, J. A.; Gale, R. W.; Schwartz, T. R. (1990). A New Approach for the Cleanup of Organic Contaminants: Polymeric Film Dialysis in Organic Solvent Media. J. Assoc. Off. Anal. Chem. 73, 290-293.]. However, the concentrated final extract still includes about 4-5% of co-extracted triolein. Subsequent purification of the extract is effected using silica chromatography, followed by exclusion chromatography to remove triolein residues interfering with the analysis. In addition to blocking a major working surface in the laboratory, simultaneous processing of a number of samples implies a high input of time and labor. Moreover, the comparatively high laboratory price for a standard SPMD 91 cm in length from EST, Inc., USA (Environmental Sampling Technologies), the only producer at present, being about 50 to 60 € apiece, represents an obstacle to systematic investigations, because substantial numbers of units would be required to this end. The use of only 10 such SPMDs would imply a financial expenditure as high as about 500-600 €.

The invention was therefore based on the object of developing a low-cost, efficient method for routine use, which method would simplify and significantly shorten said dialytic recovery of foreign substances, e.g. low-molecular weight inorganic and/or organic pollutants in environmental monitoring, from semipermeable membranes.

The invention is carried out in accordance with the claims. Surprisingly, foreign substances or pollutants can be recovered by dialysis much more rapidly from semipermeable membranes of varying length and dimensions when using a PLE (pressurized liquid extraction) apparatus. To this end, the foreign substance-loaded semipermeable membrane to be dialyzed is fixed in a netlike mask of inert materials in an extraction cartridge of the PLE apparatus. Dialysis is performed with an organic solvent or mixture of solvents, optimizing the operating variables solvent, pressure, temperature, and number of time-dependent extraction steps of the PLE apparatus.

By virtue of the present invention, a modern extraction device for performing dialyses, specifically constructed for extracting pollutants from environmental matrices and other matrices, is provided for the first time. To avoid adhering of the tube to the inner wall of the cartridge, which would hamper efficient dialysis, the semipermeable membrane is incorporated in the netlike mask of inert materials in the extraction cartridge.

In principle, so-called semipermeable passive samplers in the meaning of the invention are all those systems known from the prior art which consist of semipermeable membranes of varying length and dimensions. In one preferred embodiment they assume the form of a tube. In principle, however, other forms such as bag-shaped or pouch-shaped embodiments can also be used. Semipermeable passive samplers are also understood to be materials which include foreign substances or pollutants for the purpose of purifying a pollutant extract from higher-molecular weight matrix components and are embedded in semipermeable membranes of varying length and dimensions.

In addition to improved methodical standardization, the advantages of this method can be seen in an enormous reduction in time of previous conventional dialysis methods from 48 hours down to a static time of dialysis of <2 hours, and as a rule, preferably about 40 minutes. The capability of using semipermeable membranes of varying length and dimensions leads to a significant decrease in the consumption of solvent and to savings of material cost, because SPMDs shorter than those commercially available at present, with a length of 91 cm, can also be used and dialyzed efficiently.

The retrieval rates of the method according to the invention correspond to those achieved by means of the conventional dialysis method previously used. In fact, a significant increase of the retrieval rate from 80 to 90% was achieved in the HCH group in particular. Such improvements permit routine use of the method according to the invention.

The method of pressurized liquid extraction (PLE) is per se known. To perform said method, various apparatus are available on the market, by means of which the so-called accelerated solvent extraction can be performed to extract solid and pasty samples. Thus, one well-known manufacturer is the American company Dionex which has the company name Dionex GmbH in Germany and, among other things, has the extraction apparatus ASE 200 and ASE 300, as well as ASE 100 (as from May 2002) on the market (ASE®=accelerated solvent extraction). These apparatus allow the use of solvents of most various polarities, alone or in mixture. The extraction temperatures can be adjusted in a range of from room temperature up to 200° C. at pressures of between 3.5 (required initial pressure to operate the apparatus) and 20 MPa, the pressure merely having the function of maintaining the employed solvent in liquid state during the extraction process. A sample carousel offers the opportunity of performing 24 previously prepared extraction processes in immediate succession via a PC control device. For extraction processes, the extraction apparatus ASE 200 provides stainless steel cartridges having a capacity of 1, 5, 11, 22 and up to a maximum of 33 ml, and cartridges up to a maximum of 100 ml in the ASE 300 and ASE 100.

According to the invention, the operating variables solvent, pressure, temperature, and number of time-dependent extraction steps were optimized to meet the requirements of dialysis.

Compared to the previously applied dialysis method, the method of the invention achieves comparable recovery values within substantially shorter periods of dialysis, without impairing the quality of the membrane passive sampler (influence on pore size or dissolution of tube components).

In a preferred embodiment of the invention the pollutant-loaded membrane is a semipermeable membrane wherein the pollutants are present accumulated on an absorbent or adsorbent. Preferred is an SPMD including at least one hydrophobic absorbent or adsorbent of high accumulative capacity for semivolatile organic pollutants. Absorbents or adsorbents having high accumulative capacity are well-known to those skilled in the art. It is possible to use the well-known liquid fatty acid ester triolein (in case of lipophilic pollutants), but also, solid organic absorbents or adsorbents such as Lichrolut® (copolymer, Merck, Darmstadt, DE), XAD® (adsorber resin, Serva, Heidelberg, DE), Tenax® (polymer, Supelco, Taufkirchen, DE), silicone and/or active carbon, and materials having comparable hydrophobicity can be included as absorbents or adsorbents in a semipermeable passive sampler.

Alternatively, a membrane made of low-density polyethylene can also be an SPMD having sediment, soil, old waste, vegetable or other matrices contaminated in particular with low-molecular weight pollutants placed therein. Such placing is preferably effected by mechanical opening of the membrane, filling in the material, and subsequent sealing e.g. by means of a thermosealed seam.

According to the invention, this variant results in an improved cleanup of polluted materials. Pure extracts free of higher-molecular weight matrix-dependent interfering substances are obtained, which allow a more sensitive analysis than heretofore. An absorbent or adsorbent is not required.

Brief Description of Drawings:

In a preferred embodiment of the invention the netlike mask that is used for the semipermeable membrane is made of metal or ceramics, more preferably of stainless steel. The netlike mask, having the shape and size of the cartridge, ensures optimal and reproducible fixing of the membrane (cf., FIG. 1, SPMD tube (1) in front of a metal mask of stainless steel (2)), with no contact between the membrane and the inner wall of the extraction cartridge. FIG. 2, from the left to the right, illustrates a preferred metal net (3) with the membrane inserted therein, the insertion of the metal net into the cartridge (4) that is used, and the cartridge re-sealed with membrane and metal net (5) for the dialysis process. The close-meshed stainless steel net preferably used to this end consists of stainless steel 1 mm in thickness. Flooding of the membrane with the dialysis solvent is ensured in an optimal fashion.

Figure 1:
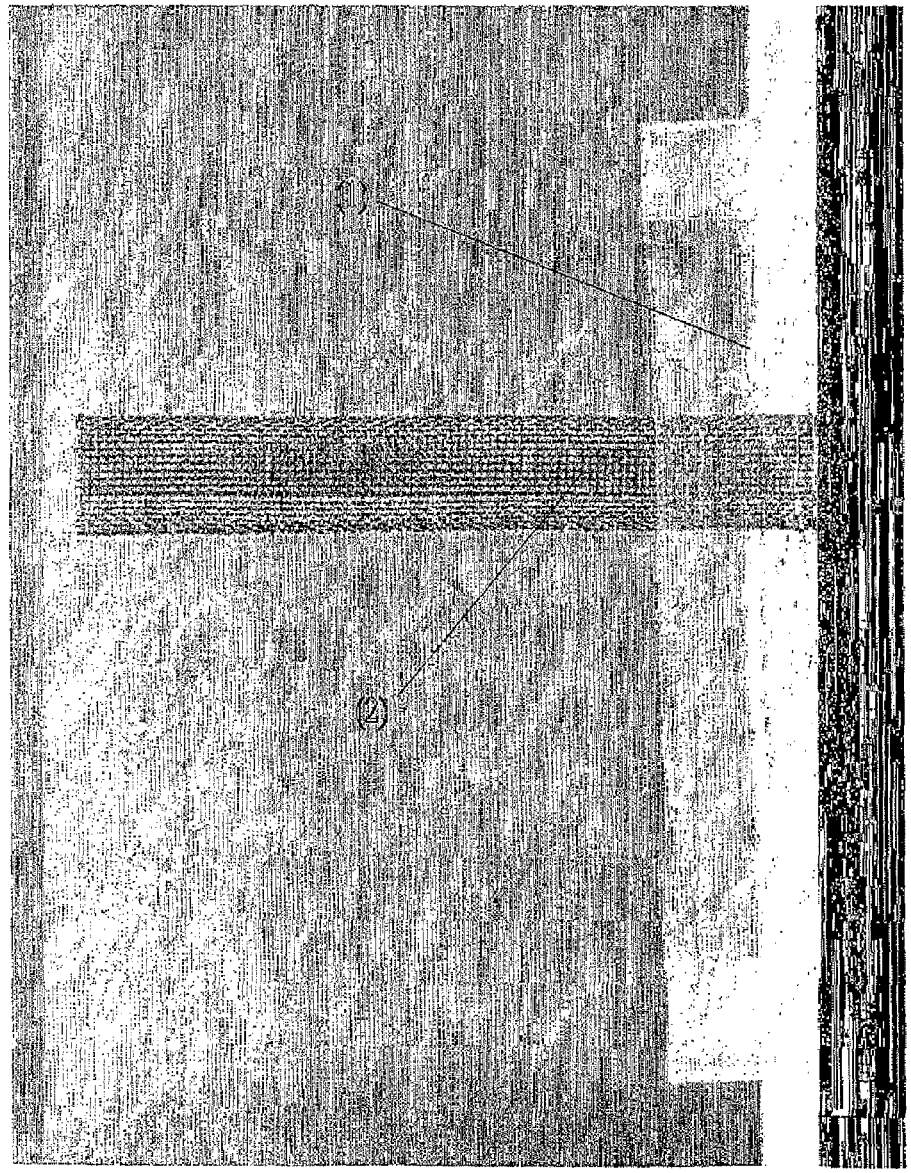
FIG. 1 shows a SPMD tube in front of a metal mask of stainless steel.
Figure 2:
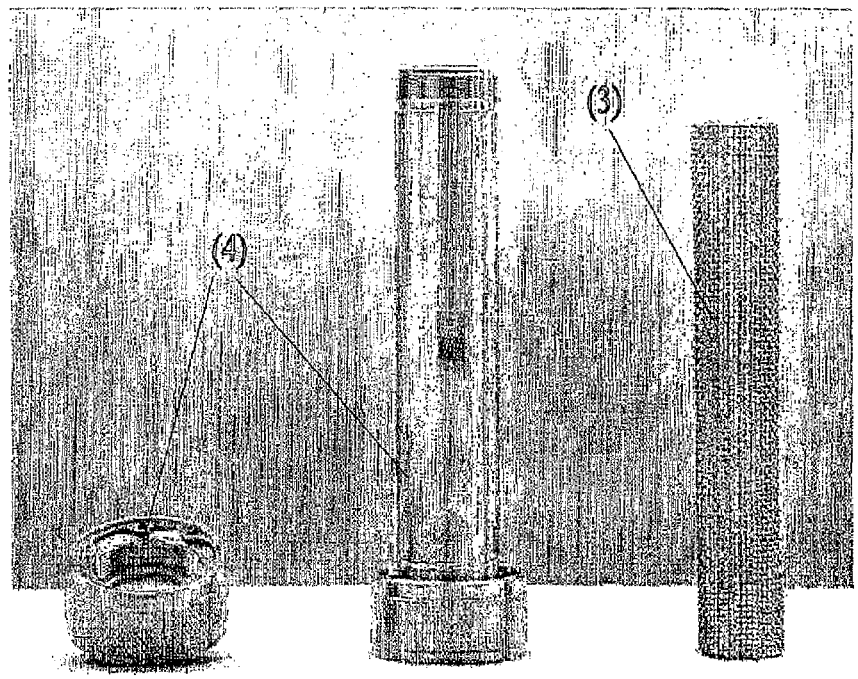
FIGS. 2 a) and b) show the metal net and cartridge and the metal net within the cartridge, respectively.
Figure 2:
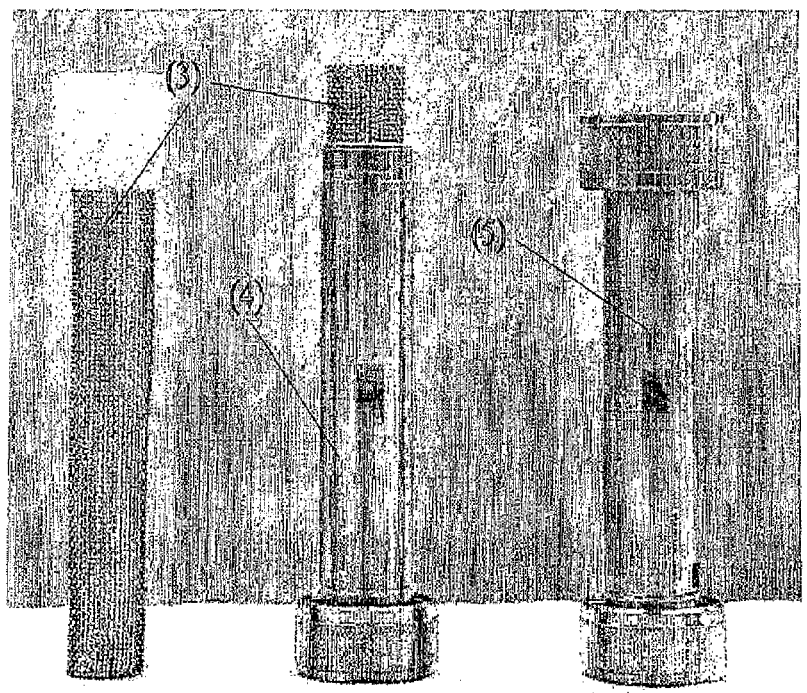

For dialytic recovery, the PLE extraction equipment that is used is adjusted in its extraction parameters, i.e., pressure, temperature, solvent, as well as number and duration of the static extraction steps, in such a way that soluble higher-molecular weight substances (molecular weight >600 g/mol) included inside the membrane would not be co-dialyzed at all, or optionally to only a very small extent (for example, triolein up to 5%). Dialysis is carried out at a pressure in the PLE apparatus which is higher than atmospheric pressure, and in a preferred fashion the pressure is adjusted to about 3.5 MPa.

The temperature in the PLE apparatus is adapted to the durability properties of the semipermeable membrane, and in a particularly preferred fashion the dialysis proceeds at room temperature and up to 50° C.

Preferred solvents are nonpolar organic solvents or a mixture of well-miscible nonpolar and polar solvents, such as n-hexane or toluene, as well as mixtures of cyclohexane and ethyl acetate, cyclohexane and acetone, n-hexane and dichloromethane, n-hexane and dichloromethane and n-hexane/and acetone. A solvent mixture of n-hexane and acetone at a ratio of from 90:10 to 50:50 was found to be particularly advantageous in the dialysis of semipermeable passive samplers (see Table 1). While in the preferred variant of using a commercially available SPMD with triolein it has been noted that the efficiency of dialysis decreases when using a higher amount of polar acetone in the mixture (e.g. n-hexane/acetone 50:50), there is a simultaneous decrease in the lipid content of triolein from 4.5% (10% acetone) via 2.5% (30%) and down to 0.8% (50%) when increasing the amount of acetone in the dialysis extract.

TABLE 1

Solvent dependence of recovery values (all figures in %)

| substance | n-hexane | n-hexane/acetone 90:10 | n-hexane/acetone 70:30 | n-hexane/acetone 50:50 |
|---|---|---|---|---|
| α-HCH | 74 | 89 | 88 | 58 |
| β-HCH | 88 | 90 | 81 | 87 |
| γ-HCH | 81 | 119 | 114 | 75 |
| δ-HCH | 87 | 90 | 81 | 85 |
| HCBz | 88 | 107 | 110 | 62 |
| PCB 28 | 82 | 113 | 113 | 84 |
| PCB 52 | 135 | 105 | 101 | 79 |
| PCB 101 | 101 | 99 | 95 | 85 |
| PCB 138 | 107 | 98 | 94 | 91 |
| PCB 153 | 106 | 98 | 94 | 90 |
| PCB 180 | 120 | 99 | 91 | 91 |
| Phen | 98 | 130 | 130 | 78 |
| Ant | 93 | 110 | 110 | 68 |
| Fluor | 96 | 114 | 115 | 91 |
| Pyr | 93 | 114 | 110 | 90 |
| BaP | 76 | 99 | 84 | 85 |

In case of deficiencies in the analysis when determining analytes at a lipid content of about 4.5% (n-hexane/acetone 90:10), the use of the 70:30 mixture with a lipid content of only 2.5% is preferred.

The time of dialysis of the static dialysis steps is substantially below 24 hours, preferably below 2 hours, but is normally no longer than 4×10 minutes.

In a particularly preferred embodiment of the invention commercially available SPMDs are dialyzed at a pressure of 3.5 MPa and at a temperature of 50° C. for 4×10 minutes, using a solvent mixture comprised of n-hexane and acetone (90:10 v/v).

The method represents an efficient and optimal solution for the dialytic recovery of pollutants from most various matrices.

The method utilizes diverse possible variations of the extraction parameters of a pressurized liquid extraction (PLE), specifically in dialytic recovery of pollutants from integrative semipermeable passive samplers, preferably from SPMDs.

The method of the invention has many advantages:

The previous dialysis method is simplified, made significantly shorter with regard to time, promoting routine use of e.g. passive samplers, preferably SPMDs, in the domain relating to the terrestrial and aquatic environment, or in workplace monitoring.

In summary, it can be stated that the invention represents a so-called "accelerated dialysis procedure" (ADP) using a pressurized liquid extraction (PLE) apparatus, wherein the variable operating parameters pressure, temperature, solvent, time of dialysis, and number of dialysis steps have been optimized. The method is preferably used to detect trace quantities of airborne organic pollutants, such as the nonpolar chloroorganic compounds HCH isomers, DDT and metabolites thereof, PCBs and PAHs, in semipermeable passive samplers.

In the dialysis of commercially available passive samplers the invention presented herein results in a considerable decrease in the time of dialysis (<2 hours, preferably 4×10 minutes instead of 48 hours), with significantly lower consumption of solvent (120 ml instead of 520 ml). This can be achieved by incorporating an inert net to fix and mechanically stabilize the semipermeable membrane in the extraction cartridge, and in this way there is optimum flooding of the membrane by the solvent during the process of dialysis in simultaneous combination with dialysis-related optimization of the operating variables. Also, merely by varying the polarity of the solvent as a result of the preferred use of said n-hexane/acetone mixture, a significant improvement of the recovery values for analytes included in the group of HCH isomers is possible without deteriorating the corresponding recovery values for analytes of other groups of pollutants.

By virtue of the present invention, the use of a modern extraction apparatus for performing dialyses, specifically constructed for extracting pollutants from environmental matrices and other materials, is possible for the first time.

In addition to improved methodical standardization, the advantages of this method can be seen in an enormous reduction in time compared to previous conventional dialysis methods, a significant decrease in the consumption of solvent, and in saving of material cost. The retrieval rates correspond to those achieved by means of the conventional dialysis method previously used. In fact, a significant increase of the retrieval rate from 80 to 90% was achieved in the HCH group in particular. Such improvements permit routine use of this method.

Moreover, PLE apparatus in combination with the dialysis method according to the invention can also be used for accelerated dialysis in other fields of application using semipermeable membranes, e.g. in the dialysis of foreign substances from medical, biochemical, biological, and technical processes.

EXAMPLE

The dialysis method was performed under the following conditions in an ASE 200 extraction apparatus including an SPMD 10 cm in length:

Insertion of the SPMD situated in a metal net of stainless steel into a 33 ml extraction cartridge Adjustment of optimum pressure: 3.5 MPa Adjustment of optimum temperature with no damaging effect on the SPMD material: 50° C.

Dialysis solvent mixture with optimum effect: n-hexane/acetone 90:10 at a maximum lipid content of 4.5% (triolein)

Optimum time of dialysis for high recovery values: 4×10 minutes, using 30 ml of fresh solvent each time The results of quintuple determinations under such optimized conditions are listed in Table 2. The mean values of HCHs were in the range of from 88% for δ-HCH and up to 100% for γ-HCH, 106% for hexachlorobenzene, about 100% for PCBs and PAHs. The RSD values, ranging between 5.1 and 19.0%, are deemed acceptable, particularly since the tests were performed at substantial time intervals, using spiked pollutant concentrations.

TABLE 2

Recovery values of optimized accelerated dialysis (solvent: n-hexane/acetone 90:10, pressure: 3.5 MPa, temperature: 50° C.)

| substance | recovery [%] | | | | | mean [%] | RSD [%] |
|---|---|---|---|---|---|---|---|
| | 1 | 2 | 3 | 4 | 5 | | |
| α-HCH | 85 | 90 | 96 | 89 | 103 | 93 | 10.8 |
| β-HCH | 83 | 95 | 96 | 90 | 95 | 92 | 12.0 |
| γ-HCH | 85 | 94 | 97 | 119 | 103 | 100 | 19.0 |
| δ-HCH | 77 | 91 | 80 | 90 | 102 | 88 | 13.6 |
| HCBz | 109 | 120 | 106 | 107 | 89 | 106 | 16.0 |
| PCB 28 | 112 | 122 | 110 | 113 | 87 | 109 | 11.9 |
| PCB 52 | 105 | 118 | 107 | 105 | 93 | 106 | 12.3 |
| PCB 101 | 104 | 112 | 95 | 99 | 111 | 104 | 8.7 |
| PCB 138 | 99 | 110 | 97 | 98 | 102 | 101 | 8.9 |
| PCB 153 | 98 | 104 | 100 | 98 | 95 | 99 | 5.1 |
| PCB 180 | 93 | 102 | 98 | 99 | 97 | 98 | 5.1 |
| Phen | 123 | 134 | 121 | 130 | 105 | 123 | 14.6 |
| Ant | 100 | 92 | 87 | 110 | 95 | 97 | 13.4 |
| Fluor | 118 | 127 | 116 | 114 | 100 | 115 | 13.0 |
| Pyr | 116 | 124 | 112 | 114 | 90 | 111 | 18.9 |
| BaP | 82 | 84 | 85 | 99 | 93 | 89 | 11.2 |

The invention claimed is:

1. A method for the dialytic recovery of a foreign substance from a passive sampler, comprising
performing dialysis with a solvent or a mixture of solvents with a pressurized liquid extraction apparatus,
which apparatus comprises an extraction cartridge in which a semipermeable passive sampler loaded with a foreign substance is fixed in a netlike mask of an inert material,
wherein the semipermeable passive sampler comprises semipermeable membranes of varying lengths and dimensions.

2. The method according to claim 1, wherein the passive sampler is tubular in shape and includes at least one hydrophobic absorbent or adsorbent of high accumulative capacity for semivolatile organic pollutants.

3. The method according to claim 2, wherein the absorbent or adsorbent of high accumulative capacity is triolein, Lichrolut, XAD, Tenax, silicone, and/or active carbon.

4. The method according to claim 2, wherein the absorbent or adsorbent of high accumulative capacity is triolein.

5. The method according to claim 2, wherein the absorbent or adsorbent of high accumulative capacity is silicone and/or active carbon.

6. The method according to claim 2, wherein the absorbent or adsorbent of high accumulative capacity is a copolymer, polymer or resin.

7. The method according to claim 1, wherein the netlike mask consists of metal or ceramics.

8. The method according to claim 1, wherein the dialysis is carried out at a pressure in the pressurized liquid extraction apparatus which is higher than atmospheric pressure.

9. The method according to claim 1, wherein the temperature is 60°C. at maximum.

10. The method according to claim 1, wherein the solvent is n-hexane, toluene, a mixture of cyclohexane and ethyl acetate, a mixture of cyclohexane and acetone, a mixture of n-hexane and methylene chloride, a mixture of n-hexane and dichloromethane, or a mixture of n-hexane and acetone.

11. The method according to claim 10, wherein a solvent mixture of n-hexane and acetone at a ratio between 90:10 and up to 50:50 is used in the dialysis of semivolatile to low volatile organic pollutants.

12. The method according to claim 1, wherein semivolatile to low volatile organics are dialyzed for at least 4×10 minutes.

13. The method according to claim 1, wherein the foreign substance is a pollutant from environmental monitoring or from medical, biochemical or biological sector.

14. The method according to claim 1 wherein the foreign substance is sediment, soil, old waste, or vegetable matrix.

15. The method according to claim 1, wherein the dialysis is carried out at a pressure of 3.5 Mpa in the pressurized liquid extraction apparatus.

16. The method according to claim 1, wherein the temperature is between room temperature (20°C.) and 50°C.

17. The method according to claim 1, wherein the temperature is at room temperature (20°C.).

18. The method according to claim 1, wherein the foreign substance is a low-molecular weight pollutant.

19. The method according to claim 1, wherein the semipermeable passive sampler consists of semipermeable membranes of varying lengths and dimensions.

20. The method according to claim 1, wherein the netlike mask comprises a metal or ceramic matrial.

21. The method according to claim 1, wherein the netlike mask is made of stainless steel.

* * * * *

UNITED STATES PATENT AND TRADEMARK OFFICE
CERTIFICATE OF CORRECTION

PATENT NO.       : 7,449,115 B2
APPLICATION NO.  : 10/512543
DATED            : November 11, 2008
INVENTOR(S)      : Wenzel et al.

It is certified that error appears in the above-identified patent and that said Letters Patent is hereby corrected as shown below:

Title page, item (73) reads "Assignee: UFZ-Umweltforschungs Zentrum Leipzig-Halle GmbH, Leipzig (DE)" should read Assignee: --HELMHOLTZ-ZENTRUM FUR UMWELTFORSCHUNG GMBH, LEIPZIG, GERMANY--

Signed and Sealed this
Fifth Day of July, 2011

David J. Kappos
*Director of the United States Patent and Trademark Office*